United States Patent [19]

Amidon et al.

[11] Patent Number: 5,455,286

[45] Date of Patent: Oct. 3, 1995

[54] BIOACTIVE COMPOSITION

[76] Inventors: Gordon L. Amidon, 2079 S. 7th St., Ann Arbor, Mich. 48103; Ramachandran Chandrasekharan, 4448 Swiss Stone Ln., Ypsillenti, Mich. 48197; Arthur H. Goldberg, 143 Montclair Ave., Montclair, N.J. 07042

[21] Appl. No.: 284,171

[22] Filed: Aug. 2, 1994

Related U.S. Application Data

[60] Continuation of Ser. No. 4,584, Jan. 14, 1993, abandoned, which is a division of Ser. No. 772,511, Jun. 27, 1991, Pat. No. 5,221,698.

[51] Int. Cl.$^6$ ............................ A01N 25/34; A01N 25/00
[52] U.S. Cl. ...................... 523/122; 514/944; 424/403; 424/405; 424/480; 424/407; 424/409; 424/418; 424/465; 424/474; 424/477; 424/478; 427/4; 427/336; 427/340; 427/341; 427/2.31
[58] Field of Search ...................... 523/122; 514/944; 424/403, 405, 480, 407, 409, 418, 465, 474, 477, 478; 427/2, 4, 336, 340, 341

[56] References Cited

U.S. PATENT DOCUMENTS 3,920,436  2/1975  Janssen ............................. 71/65

FOREIGN PATENT DOCUMENTS 0143297  6/1985  European Pat. Off. ............... 424/418

*Primary Examiner*—Paul R. Michl
*Assistant Examiner*—LaVonda R. DeWitt

[57] ABSTRACT

An improved bioactive agent delivery composition and method of application are described. The composition comprises a bioactive agent, a hydrophilic polymer in an incompletely hydrated state and a substantially water-miscible solvent system. The agent and polymer are essentially dissolved in the solvent system to form a sprayable composition having a viscosity of less than 350 cP. Upon dilution with water, the viscosity of the composition increases to in excess of 1000 cP to produce a retentive coating at the site of application which provides enhanced bioavailability of the agent.

20 Claims, 14 Drawing Sheets

BIOACTIVE COMPOSITION

This is a continuation of divisional application Ser. No. 08/004,584 filed Jan. 14, 1993, now abandoned, which is a division of application Ser. No. 07/772,511 file Jun. 27, 1991, now U.S. Pat. No. 5,221,698.

BACKGROUND OF THE INVENTION

This invention relates generally to methods and compositions for applying a bioactive agent to a surface upon which enhanced bioeffect is desired.

Myriad fields benefit substantially from a bioactive agent-containing composition having a low viscosity which permits the use of conventional spraying equipment for application. For example, certain pesticides and herbicides which are employed in the protection of plant life are easily applied by spraying equipment. However, rapid run-off of the low viscosity material results in the need for a high frequency of spraying, with corresponding increase in cost, effort, and environmental damage. There is clearly a need for a delivery method which provides increased retention of the composition on protected surfaces such as the leaves of foliage.

A similar need exists for foods. For example, certain ingestibles can be protected with a coating which is conveniently applied in liquid form by spraying. The coating may reduce the effects of air on the ingestible substance through incorporation of protective bioactive agents, such as preservatives. These sprayable compositions, however, generally drain-off or are absorbed into such foods. The protective effect of the initial coating is thereby limited.

There is additionally a need for increasing the retention of bioactive agents which are commonly applied to surfaces of the bodies of living beings. They include, for example, various forms of therapeutic drugs, cosmetic agents, sun screens, insect repellents, etc. In many instances, it is desired that a liquid form of such materials be applied, especially by spray, and that the material be retained on the substrate to increase the duration of its effectiveness.

Of all these foregoing needs, by far the most complex problems relate to the administration for many drugs. Similarly, this is the field which has received the most attention. In most instances, however, the attention has been narrowly focused and incompletely successful.

For example, extensive research on the bioavailability of orally administered drugs indicates that there is a need to explore alternative modes of administration for many of them. First-pass metabolized drugs, for example, exhibit low bioavailability when administered orally. This result may be circumvented by nasal administration, with resultant absorption through the mucosa directly into the bloodstream. Nasal sprays are, therefore, an alternative route of administration for such bioactive agents.

A serious disadvantage of this form of administration is that the solutions tend to drain rapidly into the oral cavity, causing severe losses of drug. Such losses substantially reduce the bioavailability of a drug dose. There is therefore a need for a method for delivering drugs to the body of a living being, illustratively intranasally, wherein drainage of the drug is minimized.

Application by spraying a fluid containing a bioactive agent such as a therapeutic drug onto the desired site of application is an extremely convenient form of drug administration. Often there is a need, however, to prolong the residence time of a drug at a site of application so that the extent of drug absorption is elevated. Additionally, prolongation of the residence time is desired to increase the drug bioavailability and sustain the drug's action.

Another means for applying such drugs is in gels and/or ointments. Gels and ointments have the capacity to reside for a greater time at a site of application than a sprayable fluid. Gels and ointments, however, have three major disadvantages: inconvenience of use, particularly for chronic administration; inconsistency in the amount of drug applied in any given application and reduced area of contact. Thus, there is a need for a delivery method and bioactive composition which can be sprayed or otherwise applied to body cavities both consistently and easily using commercial mechanical systems.

INTRODUCTION TO THE INVENTION

It is an object of this invention to provide a simple and inexpensive method for applying a predetermined bioactive agent to a substrate or surface.

It is another object of this invention to provide a bioactive composition having low viscosity, whereby it can be sprayed or otherwise applied using commercial mechanical systems.

It is also an object of this invention to provide a bioactive composition which can exhibit an increase in viscosity upon delivery of the bioactive agent to the desired site of application.

It is a further object of this invention to provide a bioactive composition which assists in prolonging the residence time of a bioactive agent at the site of application.

It is additionally an object of this invention to provide a method and bioactive composition for delivering a wide variety of bioactive agents in liquid (preferably aqueous) form.

SUMMARY OF THE INVENTION

It has been discovered that the foregoing and other objects can be achieved by a bioactive composition which is initially sprayable but thereafter undergoes a subsequent viscosity increase. The increased viscosity limits the extent of drainage of the bioactive agent away from the site of application, and prolongs the period of communication between the composition and the region where the effect of the bioactive agent is desired.

This invention provides, in accordance with a first aspect thereof, such a bioactive composition. This composition is characterized by a bioactive agent and a hydrophilic polymer in an incompletely hydrated state. The agent and polymer are essentially dissolved in a substantially water-miscible solvent system to produce a composition having a viscosity of less than about 350 centipoise (cP), and which increases to in excess of 1000 cP upon dilution with water.

Another aspect of the present invention relates to a method for forming a bioactive coating on a substrate. This method involves the steps of applying the foregoing bioactive composition to a substrate and diluting with water to transform the composition into a gel coating.

BRIEF DESCRIPTION OF THE DRAWING

Comprehension of this invention is facilitated by reading the detailed description which follows, in conjunction with the annexed drawings, in which.

DETAILED DESCRIPTION

Figure 1:
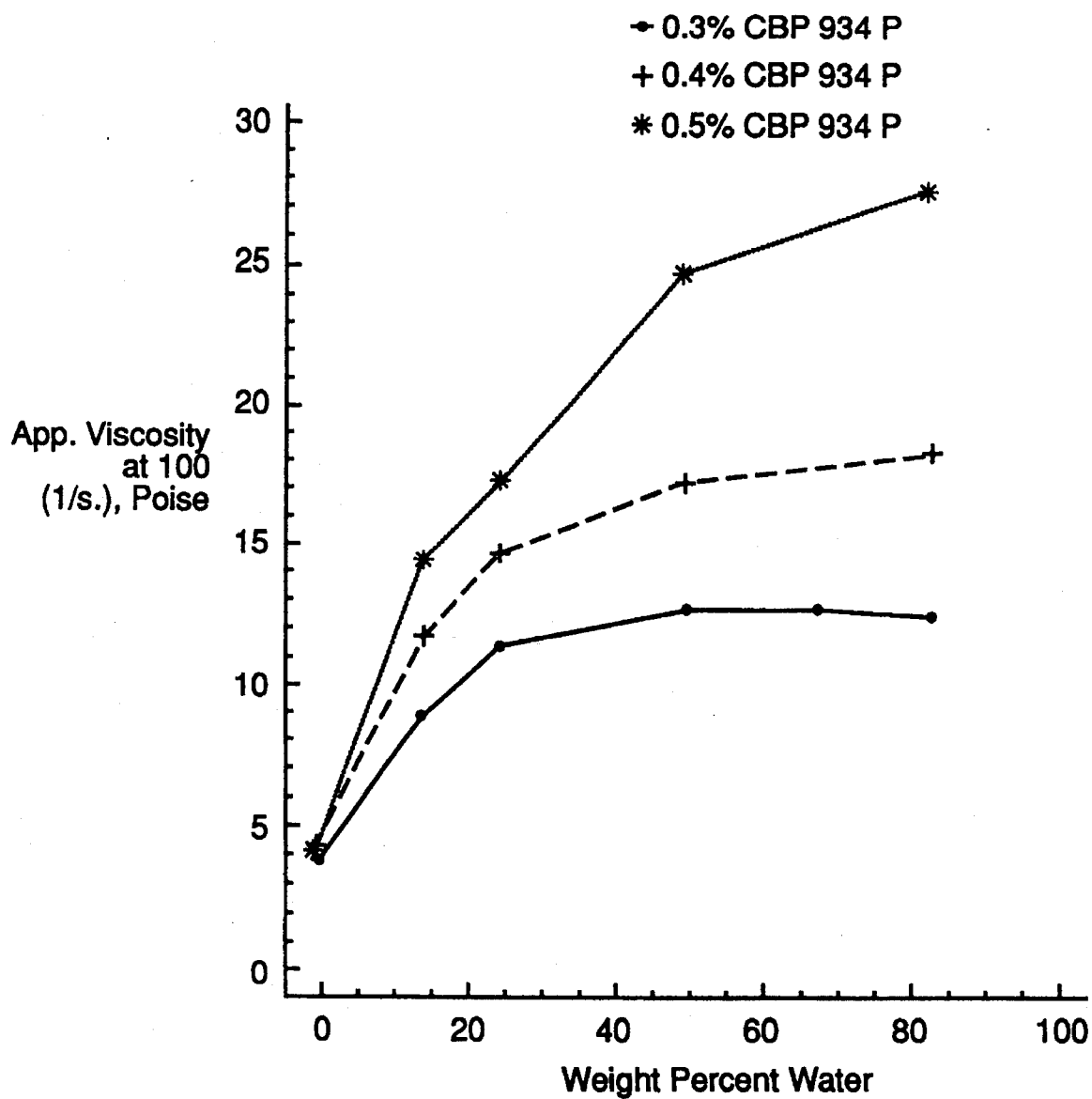
FIG. 1 is a graphical illustration showing the apparent viscosity plotted against percentage of water for three solution concentrations of a hydrophilic polymer (Carbopol 934P) in a propylene glycol-water solvent system.

The present invention is partially premised on minimizing the run-off of a liquid composition containing a predetermined bioactive agent and extending the residence time thereof at a preselected site of application. This is accomplished by causing the viscosity of the delivery composition to increase in response to the addition of moisture.

The bioactive compositions of the present invention are free-flowing liquids containing a predetermined bioactive agent and a hydratable, hydrophilic polymer essentially dissolved in a solvent system carrier. As used herein, the term "essentially dissolved" refers to any substantially homogeneous dispersion. Preferably the dispersion is a true solution, although a colloid or other liquid composition containing only minute and uniformly distributed solids will suffice.

As previously stated, the hydrophilic polymer in the present compositions should be in an "incompletely hydrated state". By this term it is meant that the polymer must be susceptible of increasing its degree of hydration. It is hydration, which occurs incident the eventual dilution of the present compositions with water, which spurs the instant increase in viscosity.

The manner in which hydration operates to cause this increase in viscosity is most readily apparent from polymer configuration. Initially, the polymer in the present solvent systems assumes a coiled form which is believed to result from the dominance of intra-, as opposed to inter-, molecular polymer bonding. The addition of water to the solvent system, however, causes an uncoiling of the polymer into a more linear form. In this form, it is believed that hydration substantially increases the degree of inter-molecular bonding and, incidentally, the viscosity of the diluted bioactive composition.

Commonly, the hydrophilic polymer employed in the present compositions is essentially anhydrous. Hence, it may contain no or virtually no water of hydration. In some embodiments, however, the solvent system is not anhydrous. Such a system may even contain a substantial amount of aqueous solvent, including up to 25% water by weight, dependent upon the remaining solvent and polymer selected. In these latter embodiments, the hydrophilic polymer is partially hydrated although not sufficiently for it to uncoil substantially in the manner previously discussed.

The rheological properties of the bioactive delivery composition should be such that the introduction of water causes a dramatic transition from a free-flowing fluid state into, most desirably, a viscoelastic gel (in excess of 10,000 cP). This dramatic increase in viscosity should be achievable with only a relatively minor input of water, desirably less than 40%, most desirably less than 10%, water by composition weight. Any bioactive agent which is dispersed in the composition will be entrapped within the resultant gel matrix and be retained in place for release at the site of application.

In order for the polymer to expand in the solvent, thereby resulting in an increase in viscosity or formation of a gel, it is necessary that the polymer also be essentially soluble in the solvent system after addition of water. If the polymer is not then soluble, precipitation will occur and no substantial increase in viscosity is obtained.

The choice of polymer and solvent system are, therefore, interrelated. The most important criteria for choosing these components of the present invention is the rheology of the polymer in the solvent system. Simple rheological studies can be conducted to obtain data on the rheological characteristics or the literature can be researched from published data. In this manner, a dramatic increase in viscosity can be assured upon the addition of water to the solvent system.

Any hydratable, hydrophilic polymer which is essentially soluble in the solvent system can be employed in the practice of the invention. In accordance with the principles of the invention, exemplary polymers which may be employed include, without limitation, homopolymers of acrylic acid monomer such as polyacrylic acid; copolymers of acrylic acid obtained by the copolymerization of acrylic acid as a main component with methacrylic acid, styrene, or vinyl ethers as comonomer; vinyl polymers such as polyhydroxyethyl acrylate, polyhydroxyethyl methacrylate, polyvinyl alcohol, or polyvinyl pyrrolidone; cellulose derivatives, such as the lower alkyl cellulose ethers including methyl cellulose, ethyl cellulose, propyl cellulose, hydroxyethyl cellulose, hydroxypropyl cellulose, carboxymethyl cellulose, etc. The salts of these polymers are also suitable.

In a still further embodiment of the present invention, the hydratable polymer is selected from the group consisting of homopolymers of acrylic acid monomer, copolymers of acrylic acid; vinyl polymers; cellulose derivatives; and the non-toxic, pharmaceutically acceptable salts of these polymers.

In certain advantageous embodiments of the invention, the hydrophilic polymer is ionic (either acidic or basic) and may be subjected to a neutralizing agent to form an acid:base complex or polymer salt. The polymer salt is soluble in the solvent system so that it remains essentially dissolved. This ensures that it will be deliverable in a fluid, sprayable form. However, the polymer or its salt must be susceptible of hydration so that introduction of water into the solvent system will cause the polymer salt to uncoil, thereby drastically increasing the viscosity of the system.

The term "neutralizing agent" as used herein refers to any agent which will enhance the solubility of polymer in the solvent system employed. This term does not necessarily refer to an agent for bringing the solution to a neutral pH (i.e. approximately 7). The choice of neutralizing agent depends upon whether the polymer is acidic or basic. If a neutral polymer is employed, the choice of neutralizing agent depends on whether an acidic or basic agent is required to increase polymer solubility in the particular solvent system employed.

The basic neutralizing agents of the present invention may be either an inorganic base or an organic amine. They are preferably soluble in both the non-aqueous solvent(s) and water. In certain highly advantageous embodiments, the neutralizing agent is an organic amine, especially triethanolamine. Other organic amines, such as diisopropanolamine or monoethanolamine; basic amino acids, such as arginine, lysine, or histidine; or amine surfactants, such as Ethomeens or Jeffamines (trademarks of Jefferson Chemical Co.), can be employed in lieu of triethanolamine with similar results. Of course, in embodiments where the hydrophilic polymer is basic, the neutralizing agent should be an acid, such as an inorganic acid.

In a further embodiment of the invention, the neutralizing agent is an organic amine and is selected from the group consisting of triethanolamine, diisopropanolamine, monoethanolamine, basic amino acids and amine surfactants. This agent is preferably present in an amount approximately between 0.3 and 10 percent by weight of the composition. The preferred neutralizing agent is triethanolamine.

In a particularly preferred embodiment of the invention, the acidic ionic polymer is Carbopol 934 or 934P (934P is the pharmaceutical grade of the Carbopol designated 934). Carbopol is a registered trademark of the B. F. Goodrich Company, Specialty Polymers & Chemical Div., Cleveland, Ohio 44131. Carbopol 934P, generically known as Carbomer, is a synthetic high molecular weight polymer of acrylic acid (MW 3,000,000) approved for human usage by the Food and Drug Administration. It is typically used in the pharmaceutical industry in controlled release tablets, oral suspensions, EKG gels and topical products. More specifically, Carbopol 934P is a cross-linked acrylic acid-allyl sucrose copolymer (the preparation and description of Carbopol 934/934P are reported to be set forth in U.S. Pat. Nos. 2,798,053 and 2,909,462).

In further specific embodiments, the hydrophilic polymer (most desirably Carbopol) is an acidic ionic polymer neutralized with an inorganic base and an organic amine. Preferably, the neutralizing agent is an organic amine and is selected from the group consisting of triethanolamine, diisopropanolamine, monoethanolamine, basic amino acids and amine surfactants. Alternatively, the hydrophilic polymer employed is a basic polymer, and the neutralizing agent is an inorganic acid.

The solvent system must contain a non-aqueous solvent. One or more additional solvents are provided in certain embodiments. In one practical embodiment, the first non-aqueous solvent is propylene glycol, and a second solvent is a parenteral vehicle selected from the group consisting of dimethylacetamide, ethyl lactate, ethyl carbonate, dimethylformamide, dimethyl sulfoxide, and dioxolanes.

For drug delivery embodiments, the pharmaceutically-approved compound propylene glycol is a preferred solvent. However, propylene glycol can be an irritant at high concentrations. Therefore, in particularly preferred embodiments, the propylene glycol content of the non-aqueous solvent system is limited to approximately 55 percent by total weight. This limitation requires at least a second pharmaceutically acceptable solvent which does not materially increase the viscosity of the system or adversely alter the viscoelastic properties thereof.

Rheological studies have confirmed that dimethylacetamide, a known solvent currently used in parenteral formulations, is suitable as a second non-aqueous solvent in a propylene glycol system. Systems of propylene glycol and dimethylacetamide yield results which are similar to those observed for a pure propylene glycol system. Other non-aqueous parenteral vehicles, such as ethyl lactate, ethyl carbonate, dimethylformamide, dimethyl sulfoxide, and dioxolanes are also acceptable co-solvents.

In a further embodiment, the solvent system includes an oil. This oil solvent is selected from the group consisting of hydrophobic organic substances, such as hexadecane or benzyl alcohol, and oils derived from vegetable and animal sources, including an oil selected from the group consisting of vegetable oils, fixed oils, and essential oils.

In such an embodiment, the oil may be selected from the group consisting of oils and hydrophobic organic substances, the oil being present in an amount of up to approximately 30 percent by weight of the composition. Additionally, the oil may be selected from the group consisting of benzyl alcohol, hexadecane, and olive oil, and is preferably present in an amount approximately between 2 and 25 percent by weight of the composition.

In these compositions, the solvent system may, in some embodiments, be an emulsion containing an oil phase and optional emulsifying agent. The oil of that phase may constitute any of the foregoing oils. Emulsification may be aided by the addition of a detergent or surfactant, synthetic or otherwise, which has the capacity to form micelles. The resulting non-aqueous emulsion should have a sprayable viscosity, i.e., less than about 350 cP.

Where the solvent system of the bioactive agent delivery composition is provided with an emulsifying agent, that agent is desirably a non-ionic surfactant of HLB less than about 15. Preferably, the non-ionic surfactant is selected from the group consisting of Span 80, Span 65, Span 40, Tween 80 and Tween 65.

In a preferred embodiment, the emulsifying agent may be Span 80, a sorbitan ester surfactant with an HLB of 4.3. Additionally any of many other non-ionic surfactants having a relatively low HLB (less than about 15), including without limitation, Span 65, Span 40, Tween 80 and Tween 65, may be employed in the practice of the invention.

In accordance with a further aspect of the invention, the invention contemplates a method of forming a coating on a substrate. This method comprises the steps of applying a bioactive agent and a hydrophilic polymer in an incompletely hydrated state which are essentially dissolved in a substantially water-miscible solvent system to a substrate, the composition having a viscosity of less than 350 centipoise; and diluting the composition with water, whereby the water interacts with the polymer to form a gel coating on the substrate, the gel having a viscosity in excess of 1000 centipoise.

In a specific embodiment of this method, the step of applying includes spraying the liquid composition onto the substrate. For most spray methods, commercially available mechanical applicators such as metered dose nebulizers may be used. Of course, many other types of applicators are within the contemplation of the invention. In certain embodiments, it may be necessary or desirable to control the amount of water and/or non-aqueous solvents delivered to the surface. In this situation, a dual compartment dispenser containing water in one compartment and the bioactive agent-containing composition in the other is recommended. The two compartments may be pumped separately, but simultaneously, by a single spring-loaded pump to a common nozzle or to separate nozzles. Such a dual compartment dispenser is particularly useful in a situation where the bioactive agent delivery composition is being applied to a dry surface or where an aqueous polymer system is employed to a dry surface. The importance of the characteristics of the polymer (or its neutralized salt) may be seen from the following representative study.

Representative Rheological Study

The rheological behavior of several concentrations of Carbopol 934P at various temperatures was examined in the non-aqueous solvent, propylene glycol, and in varying mixtures of water and propylene glycol. These mixtures imitate the result obtained upon aqueous dilution of a composition in accordance with the present invention wherein the solvent system is pure propylene glycol. For this rheological study, the neutralizing agent employed was the organic amine, triethanolamine. Continuous shear experiments were conducted on the various formulations using a Rheomat 135S viscometer with a concentric cylinder (cup-and-bob) attachment.

The apparent viscosities (Poise) at a shear rate of 100 per second for various concentrations of Carbopol 934P in propylene glycol and water mixtures are listed below in Table 1.

TABLE 1

| wt % water | wt % Carbopol 934P | | | | |
|---|---|---|---|---|---|
| | 0.2% | 0.3% | 0.4% | 0.5% | 0.6% |
| 0 | 2.2 | 3.4 | 4.1 | 3.8 | 4.2 |
| 10 | | 7.2 | | | |
| 15 | 3.3 | 8.5 | 11.5 | 14.5 | |
| 20 | | | | 17.0 | |
| 25 | | 11.1 | 14.6 | | |
| 50 | 4.0 | 12.3 | 17.2 | 24.7 | 32.7 |
| 85 | | 12.4 | 18.0 | 27.5 | |

It is evident from Table 1 that the apparent viscosity increases dramatically as the water content in the solvent mixture is increased. It is also evident that the rate of increase of viscosity is high at lower water concentrations and that the increase in viscosity with increasing amounts of water essentially levels off at around 50% water by weight. Almost 95% of the increase in viscosity occurs over a relatively narrow range of solvent composition.

Figure 2:
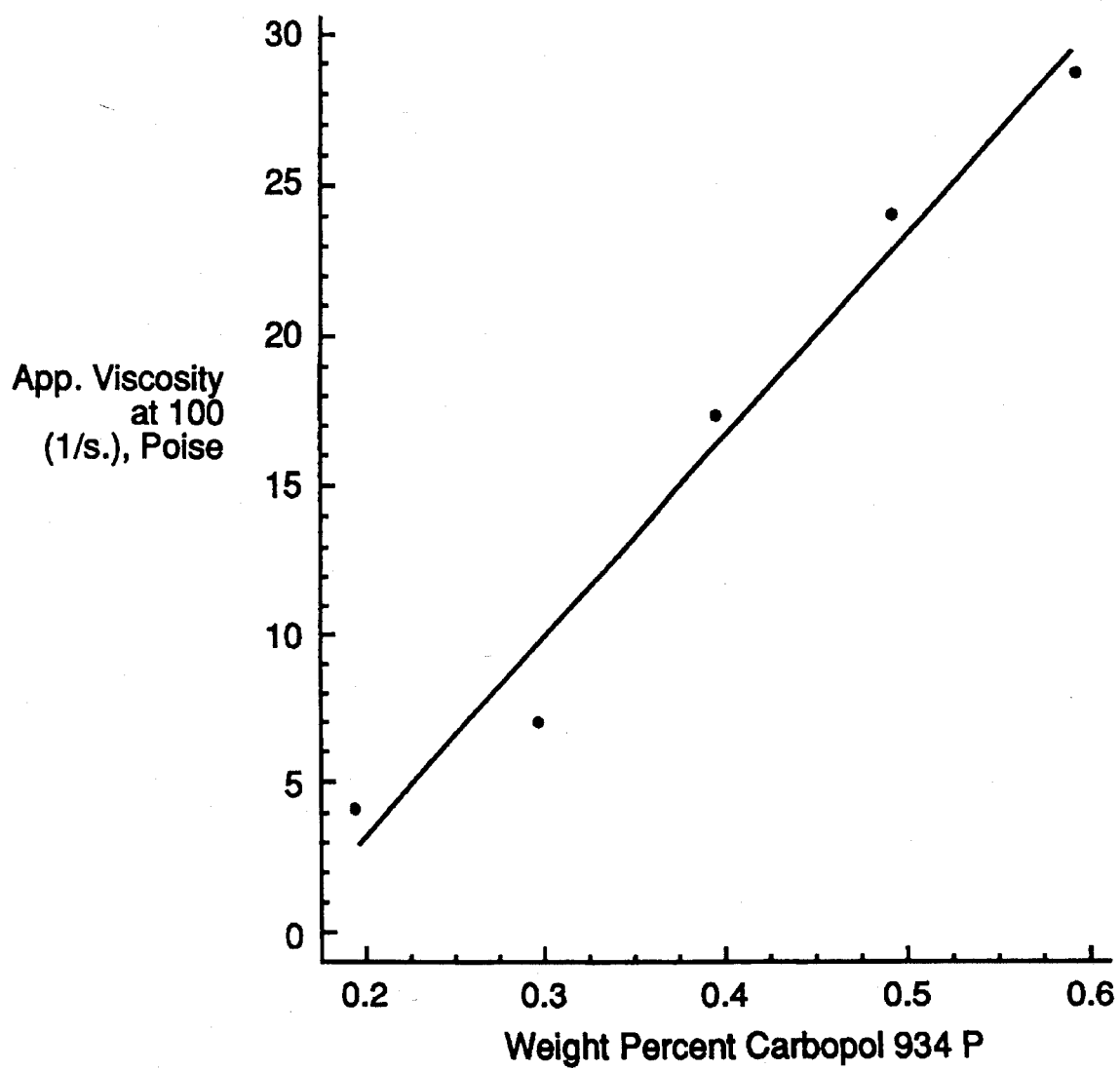
FIG. 2 is a graphical representation of apparent viscosity plotted against weight percent of Carbopol 934P in a 50%/50% propylene glycol/water mixture.

FIG. 1 is a graphical illustration showing apparent viscosity plotted against percentage of water in a propylene glycol-water system for three concentrations of Carbopol 934P (CBP 934P). The viscosities of solutions of Carbopol 934P in pure propylene glycol do not change to any significant degree with increasing Carbopol 934P concentration. However, the viscosities of water-rich mixtures increase linearly with Carbopol 934P concentration as seen in FIG. 2 which is a graphical representation of apparent viscosity plotted against weight percent Carbopol 934 P in a 50/50 propylene glycol/water mixture. The viscosities for aqueous solvent system were consistently higher than the corresponding non-aqueous propylene glycol systems. Moreover, the increase in aqueous solution viscosity over the corresponding viscosity in propylene glycol solution increased as a function of polymer concentration. It also was discovered that for a given concentration of Carbopol 934P, an increase in the water content in a mixture increased the viscosity. The increase in viscosity ranged from about two-fold for 0.2 percent Carbopol 9334P to about ten-fold for a 1.0 percent Carbopol concentration.

Figure 3:
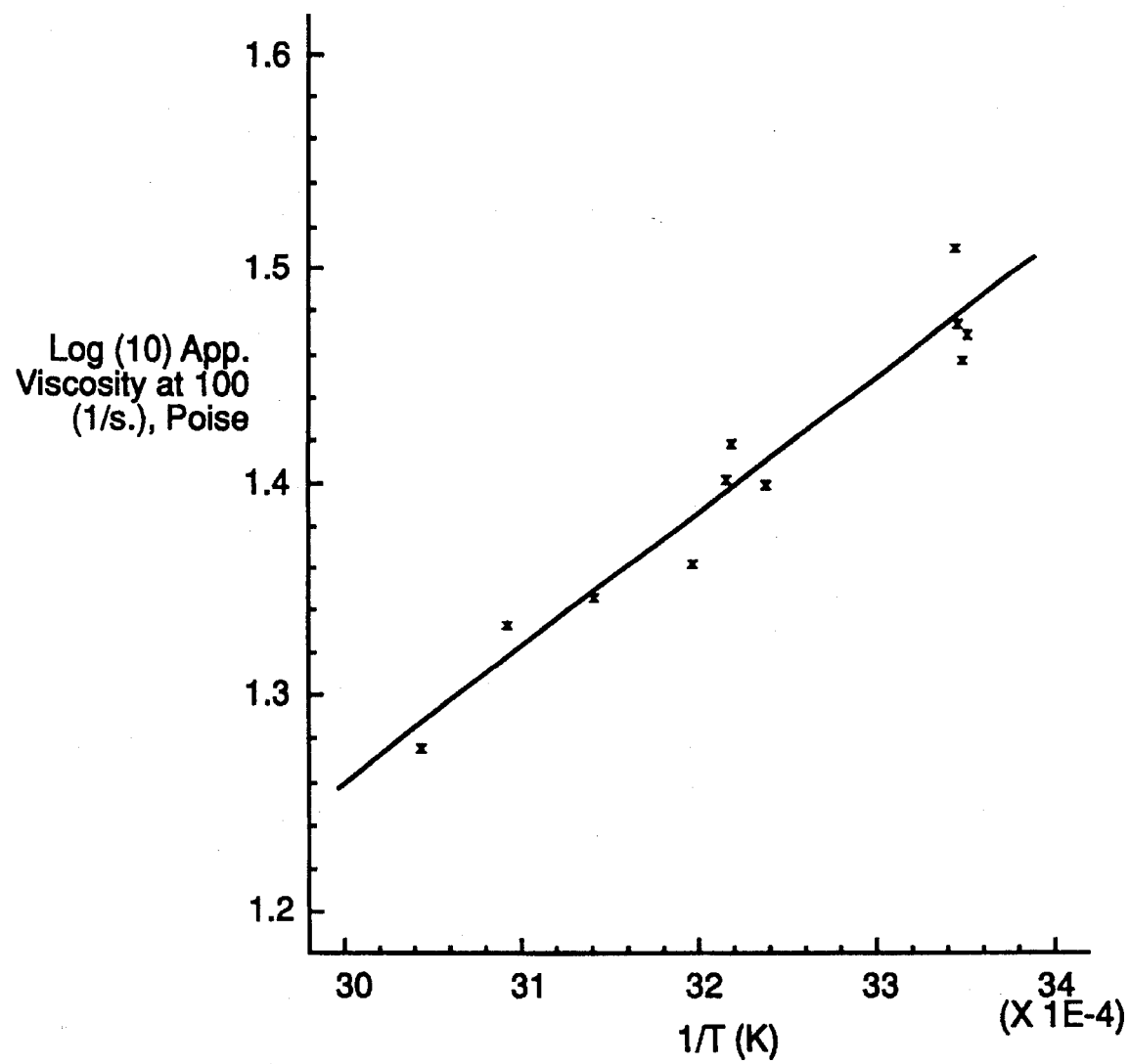
FIG. 3 shows temperature effects on apparent viscosity for the Carbopol 934P solution shown in FIG. 2.

FIG. 3 shows temperature effects on apparent viscosity for the Carbopol 934P solution shown in FIG. 2. These temperature effects are essentially minor and reversible.

The increase in viscosity upon changing solvent composition from pure propylene glycol to a water-containing system is substantial, particularly at higher concentrations of Carbopol 934P. However, higher Carbopol 934P concentrations result in a more viscous non-aqueous solution. Thus, it may be desirable to increase the fluidity of the non-aqueous propylene glycol-polymer system without forfeiting a high viscosity enhancement factor. This goal may be achieved by altering the solubility of the Carbopol 934P-triethanolamine salt in propylene glycol by the addition of chemical components which are very soluble in propylene glycol. Solubility-adjusting components may form an oil phase emulsion and comprise hyrophobic additives and/or emulsifying agents which are miscible in propylene glycol, all as previously described.

Example 1

A specific illustrative composition of the bioactive agent delivery compositions of the present invention is as follows, all percentages are by weight:

| 1.5% | Carbopol 934P | Polymer |
|---|---|---|
| 35.0% | Propylene Glycol | First Solvent |
| 42.0% | Dimethylacetamide | Second Solvent |
| 10.0% | Triethanolamine | Neutralizing Agent |
| 5.0% | Benzyl Alcohol | Oil Solvent |
| 1.5% | Span 80 | Emulsifying Agent |
| 5.0% | Bioactive Agent | Bioactive Agent |

This formulation has a viscosity of around 100–200 cP. The formulation can be delivered consistently and without difficulty using commercially available mechanical delivery systems, such as a metered dose nebulizer for intranasal delivery. Each spray from a typical nebulizer delivers a total of about 0.1 g of the formulation and, hence, about 5 mg of the bioactive agent. The density of this formulation is about 1.001 g/cc.

When the above formulation is sprayed onto a moist glass slide or other moist surfaces, it becomes a gel. Alternatively, spraying water onto the formulation after it has been applied to a dry surface causes the same gelation process to occur. Thus, this formulation will undergo a change from a free-flowing non-aqueous fluid to a gel when it is sprayed into or onto moist regions of the body, such as the nasal or oral cavities which have relative humidity on the order of 98%.

The range of operative proportions of the ingredients of the composition is extremely broad. Illustrative ranges are as follows:

| | |
|---|---|
| Hydrophilic Polymer: | 0.1% to 10% by weight of the composition |
| First Non-Aqueous Solvent: | 11% to 100% of the solvent system |
| Second Solvent: | 0% to 99% of the solvent system |
| Oil Solvent: | 0% to 30% by weight of the composition |
| Bioactive Agent: | 0.05% to 20% by weight of the composition |
| Emulsifying Agent: | 0% to 5% by weight of the composition |
| Neutralizing Agent: | 0% to 20% by weight of the composition |

The most preferred ranges of proportions of the ingredients (expressed as a percentage of weight of the total composition) for the bioactive agent delivery composition of the present invention in the context of the specific exemplary embodiment of Example 1 are as follows:

| | |
|---|---|
| Carbopol 934P | 0.60% to 2.00% |
| Propylene glycol | 30.00% to 55.00% |
| Dimethylacetamide | 30.00% to 55.00% |
| Benzyl Alcohol | 2.00% to 25.00% |
| Bioactive Agent (Drug) | 1.00% to 10.00% |
| Span 80 | 0.50% to 2.00% |
| Triethanolamine | 0.03% to 10.00% |

Persons skilled in the art will recognize that other materials may be employed as equivalents to those set forth immediately hereinabove. Such substitution materials, of course, are preferably physiologically acceptable, non-toxic, and non-irritating at use levels for drug delivery embodiments.

Several additional, illustrative embodiments of a delivery system for use with a bioactive agent in accordance with the invention are given herein below in Examples 2 and 3. These are similar in composition to Example 1, but incorporate hexadecane and olive oil, respectively, as the oil solvent instead of benzyl alcohol as set forth in Example 1.

Example 2

| | |
|---|---|
| 0.50% | Carbopol 934P |
| 42.00% | Propylene glycol |
| 28.00% | Dimethylcetamide |
| 2.00% | Hexadecane |
| 2.20% | Tween 80 |

Example 3

| | |
|---|---|
| 0.55% | Carbopol 934P |
| 39.00% | Propylene glycol |
| 28.00% | Dimethylcetamide |
| 1.40% | Olive Oil |
| 2.10% | Tween 80 |

Tables 2 and 3, below, illustrate the apparent viscosities of the compositions of Examples 2 and 3, respectively, after addition of 30% water into the non-aqueous solvent system and the enhancement factors in viscosity at various shear rates.

TABLE 2

| | Apparent Viscosity Poise | | |
|---|---|---|---|
| Shear Rate (l/s) | Before Water | After Water | Enhancement Factor |
| 20 | 1.17 | 33.11 | 28.3 |
| 40 | 0.96 | 21.58 | 22.5 |
| 60 | 0.88 | 16.83 | 19.1 |
| 80 | 0.66 | 14.33 | 21.7 |
| 100 | 0.68 | 12.57 | 18.5 |
| 120 | 0.68 | 11.34 | 16.7 |
| 200 | 0.56 | 8.53 | 15.2 |

TABLE 3

| | Apparent Viscosity Poise | | |
|---|---|---|---|
| Shear Rate (l/s) | Before Water | After Water | Enhancement Factor |
| 20 | 1.79 | 46.40 | 25.9 |
| 40 | 1.48 | 29.20 | 19.7 |
| 60 | 1.38 | 22.60 | 16.4 |
| 80 | 1.18 | 18.5 | 15.7 |
| 100 | 1.05 | 16.2 | 15.4 |
| 120 | 0.98 | 14.9 | 15.2 |
| 200 | 0.88 | 10.8 | 12.3 |

It seen from these tables that the enhancement in viscosity can as much as about thirty-fold at low shear rate. The enhancement in viscosity for the two formulations at 25° C. and 35° C. at a shear rate of 10 per second is set forth in Table 4. Apparent viscosity is a function of shear rate and this low shear rate (10 per second) is typical of ciliary beat frequencies in the nasal cavity.

TABLE 4

| | Enhancement Factor at 10 (l/s) | |
|---|---|---|
| Formulation | 25° C. | 35° C. |
| Example 2 +27% Water | 33 | 27 |
| Example 3 +30% Water | 31 | 25 |

Several additional illustrative examples of a hydrophilic polymer and non-aqueous solvent system having the appropriate rheological characteristics for use in the practice of the present invention are given below:

Example 4

| | |
|---|---|
| hydroxypropylcellulose H (HPC H) | 20 g |
| methanol qs | 1000 ml |

Example 5

| | |
|---|---|
| sodium carboxy methylcellulose (CMC) | 20 gm |
| methanol qs | 1000 ml |

Both of these compositions incorporate non-ionic polymers and exhibit increases in viscosity upon being subjected to the presence of water. The viscosity effect the presence of water is tabulated herein below:

TABLE 5

| Formulation | Amount | Viscosity CPS |
|---|---|---|
| Stock Solution: | | |
| Hydroxypropyl cellulose H | 20 gm | |
| Methanol (solvent) | 1000 ml | |
| Stock Solution | 50 ml | 2345 |
| Solvent | 50 ml | |
| Stock Solution | 50 ml | 2650 |
| Solvent | 40 ml | |
| Water | 10 ml | |
| Stock Solution | 50 ml | 2650 |
| Solvent | 30 ml | |
| Water | 20 ml | |
| Stock Solution | 50 ml | 2665 |
| Solvent | 15 ml | |
| Water | 35 ml | |
| Stock Solution | 50 ml | 3370 |
| Water | 50 ml | |
| Stock Solution | 25 ml | 225 |
| Solvent | 40 ml | |
| Water | 35 ml | |
| Stock Solution | 40 ml | 890 |
| Solvent | 25 ml | |
| Water | 35 ml | |

Figure 4:
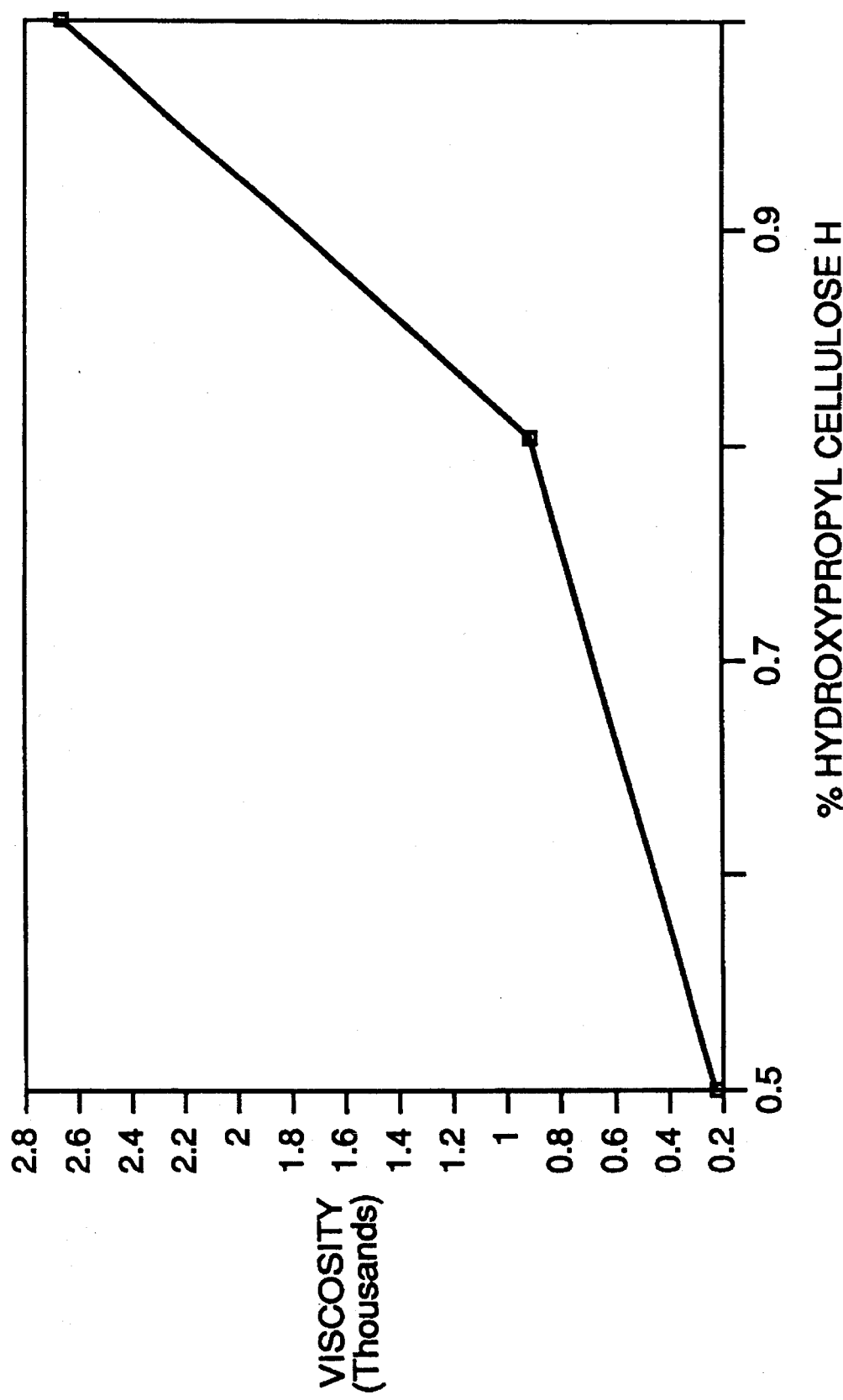
FIG. 4 is a graphical representation which illustrates the relationship between viscosity and the concentration of hydroxypropylcellulose in a solvent system comprising 64%/36% methanol/water.
Figure 5:
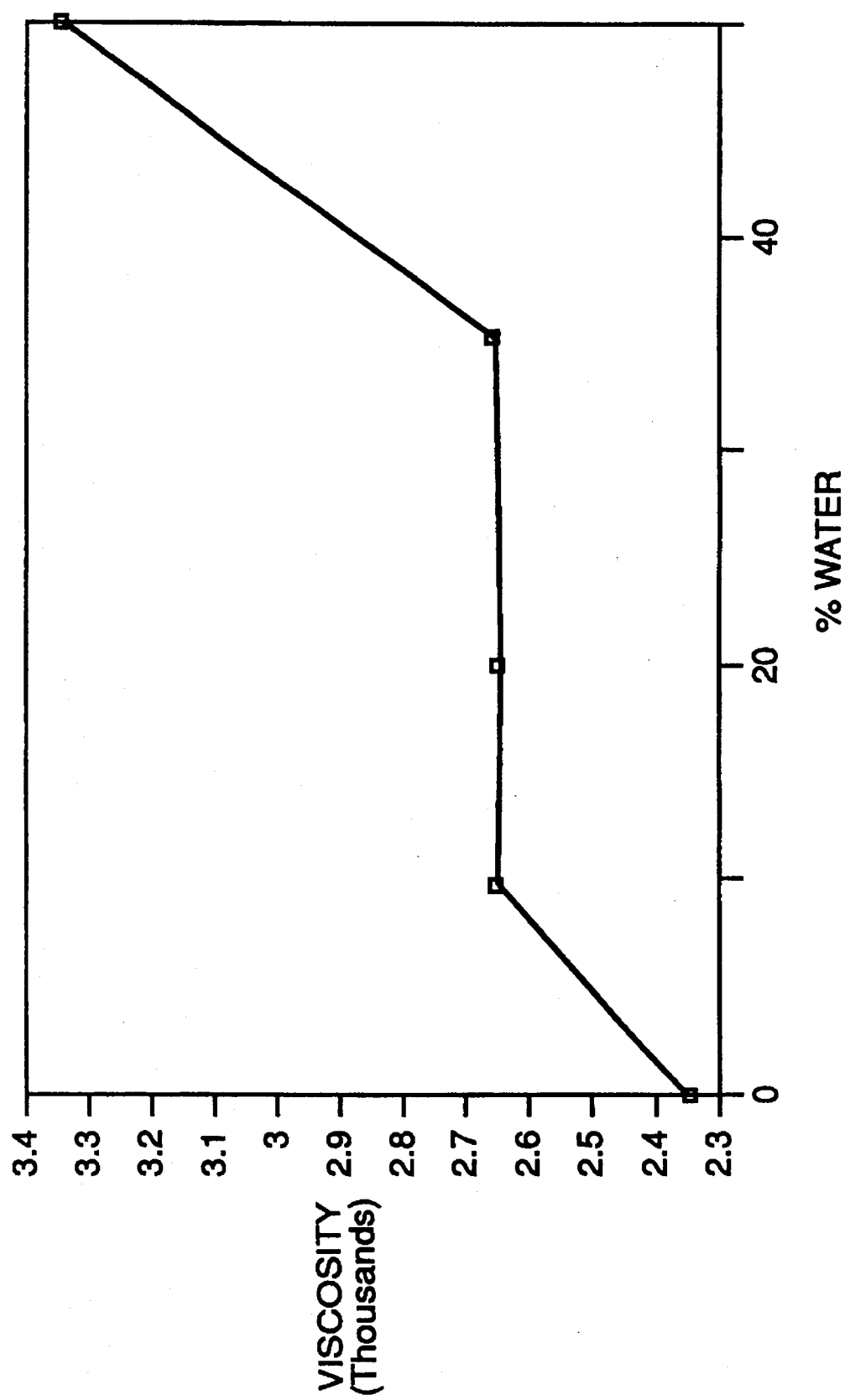
FIG. 5 is a graphical representation which illustrates the relationship between viscosity and water content for a 1% solution of hydroxypropylcellulose in a methanol/water solvent system.

FIG. 4 is a graphical representation which illustrates the relationship between viscosity and the concentration of hydroxypropyl cellulose (HPC H) in a solvent system comprising 36% water in methanol. Viscosity is seen to increase linearly for greater polymer concentrations. FIG. 5 is a graphical representation which illustrates the relationship between viscosity of a 1% solution of HPC H in methanol and the amount of water in the solvent system. A substantial increase in viscosity is observed upon introduction of greater than about 35 percent water to the solvent system.

TABLE 6

| Formulation | Amount | Viscosity CPS |
|---|---|---|
| Stock Solution (Suspension): | | |
| Sodium CMC (In Suspension) | 20 gm | |
| Methanol (Solvent or Vehicle) | 1000 ml | |
| Stock Solution | 50 ml | 8 |
| Solvent | 50 ml | |
| Stock Solution | 50 ml | 10.3 |
| Solvent | 40 ml | |
| Water | 10 ml | |
| Stock Solution | 50 ml | 11.5 |
| Solvent | 30 ml | |

TABLE 6-continued

| Formulation | Amount | Viscosity CPS |
|---|---|---|
| Water | 20 ml | |
| Stock Solution | 50 ml | 2195 |
| Solvent | 15 ml | |
| Water | 35 ml | |
| Stock Solution | 50 ml | 2585 |
| Water | 50 ml | |
| Stock Solution | 25 ml | 695 |
| Solvent | 40 ml | |
| Water | 35 ml | |
| Stock Solution | 40 ml | 1620 |
| Solvent | 25 ml | |
| Water | 35 ml | |

Figure 6:
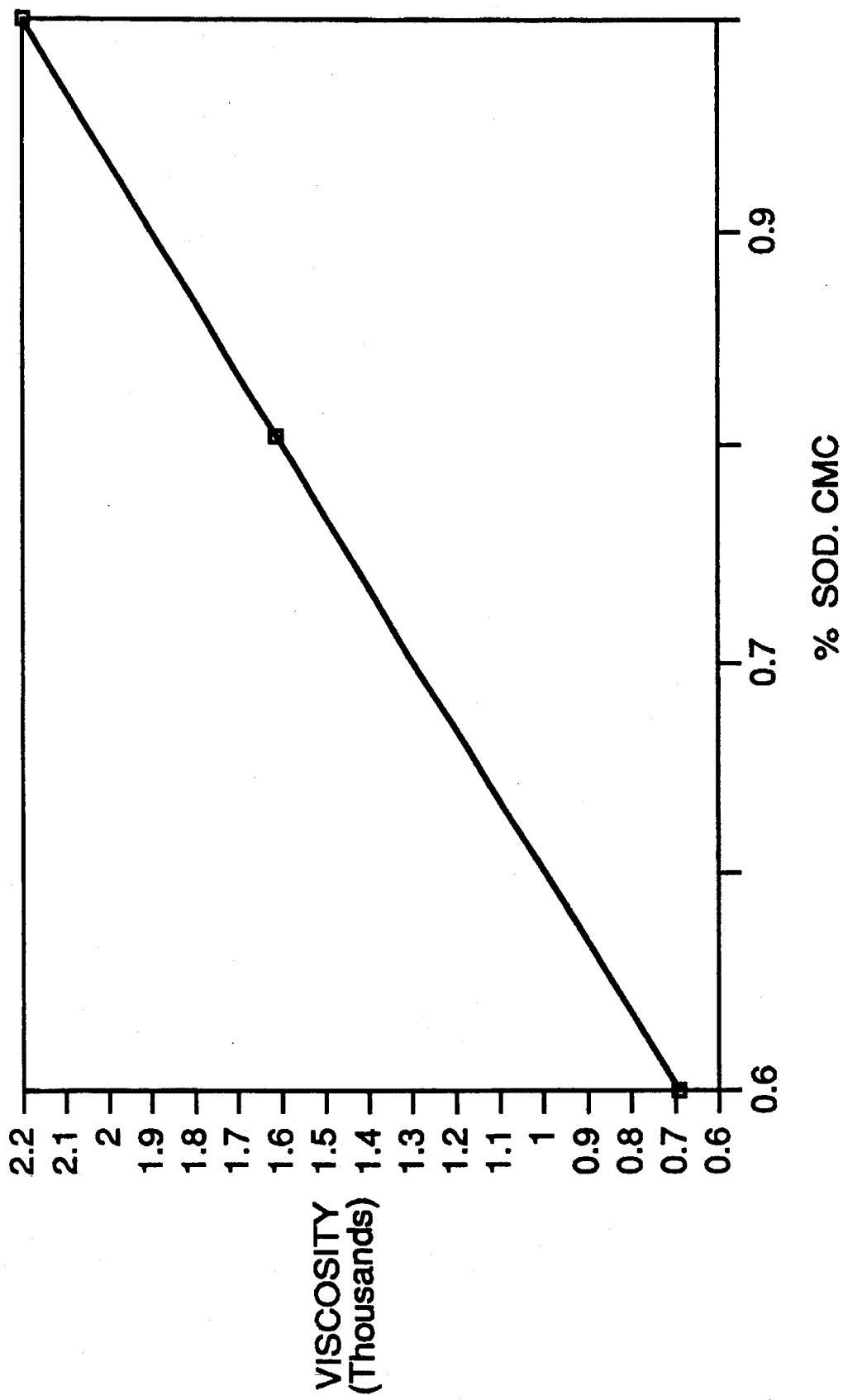
FIG. 6 is a graphical representation which illustrates the relationship between viscosity and the concentration of sodium carboxymethylcellulose in a 64%/36% methanol/water solvent system.
Figure 7:
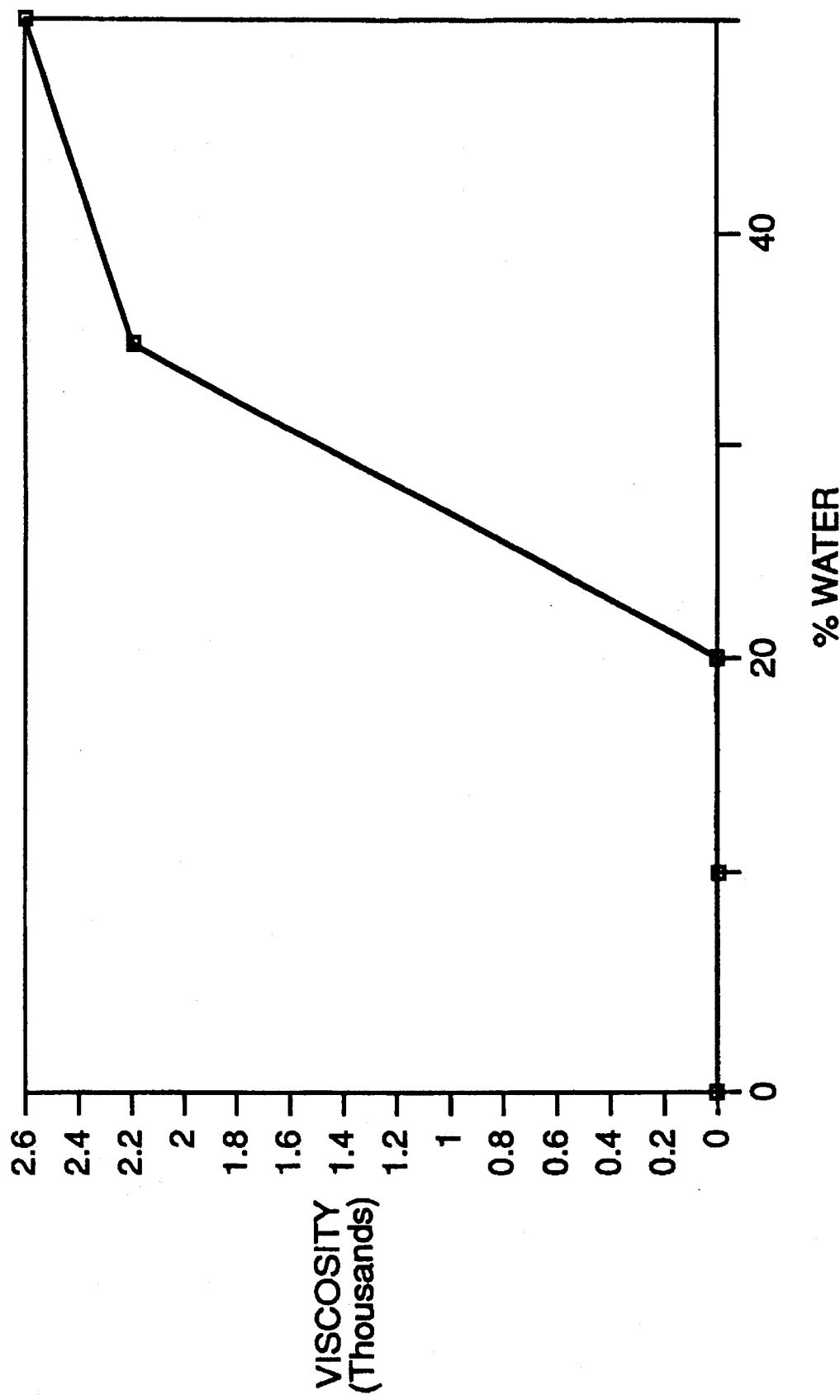
FIG. 7 is a graphical representation which illustrates the relationship between viscosity and water content for a 1% solution of sodium carboxymethylcellulose in methanol/water solvent system.

FIG. 6 is a graphical representation which illustrates the relationship between viscosity and the concentration of sodium carboxyy methylcellulose (sod. CMC) in a solvent system comprising 36% water in methanol. The viscosity is seen to increase linearly with increasing polymer concentration. FIG. 7 is a graphical representation which illustrates the relationship between the viscosity of 1% of sodium CMC suspended in methanol and the amount of water introduced into the solvent system. A substantial increase in viscosity is seen for water concentrations in excess of 20 percent.

Preparation of Bioactive Systems

In accordance with a method aspect of the invention, several illustrative modes of preparation of the bioactive system of the present invention are set forth in detail below. In general terms, the method of preparation of the non-aqueous liquid carrier or vehicle includes the steps of dissolving or otherwise dispersing the hydrophilic polymer in at least one solvent and adding a bioactive agent to the resultant dispersion. The bioactive agent may be added directly to the dispersion, or may first be first dispersed in solvent.

In embodiments where a neutralizing agent is used, the neutralizing agent is normally added to polymer in the solvent system. In certain advantageous embodiments, there is an additional step of forming an emulsion by adding an oil solvent and/or an emulsifying agent. The solution or emulsion thus formed should be a free-flowing liquid having a low viscosity of less than 350 cP, and preferably about 100 to 200 cP.

The precise mode of preparation is often contingent upon the nature of the bioactive agent being incorporated within the vehicle. For this purpose, these agents are broadly classified in three categories:

a) cationic agents, such as propranolol hydrochloride, which interact with the hydratable polymer such as the acrylic acid polymer Carbopol 934P;

b) hydrophobic agents, such as progesterone, which could alter the solubility characteristics in the non-aqueous solvent or the oil phase; and c) all other agents which are not included in category (a) or (b).

Preparation of Formulations Containing Category (a) Agents

1. Measure an appropriate amount of solvent (e.g. propylene glycol, 35–36 g) into a container and stir with a magnetic stirrer such that a vortex is formed.

2. Slowly add an appropriate amount of polymer (e.g.

Carbopol 934P, 0.5 g) into the vortex of the solvent over a period of about 5 minutes and stir continuously to maintain vortex until the polymer has dissolved.

3. Add the appropriate amount of cationic bioactive agent (e.g. propranolol hydrochloride, 5 g) to the polymer-containing solution and stir well. The system will be viscous at this state.

4. Add the appropriate amount of oil solvent (e.g. benzyl alcohol or olive oil, 4–5 g) and mix well.

5. Add the appropriate amount of neutralizing agent (e.g. triethanolamine, 10–11 g) and mix well.

6. Dissolve a small amount of polymer (1.2 g of Carbopol 934P) in a second portion of solvent (e.g. dimethylacetamide, 40 g) and add to above product of step (5).

7. Add the appropriate amount of emulsifier (e.g. Span 80, 1.1.5 g ) and mix thoroughly.

Preparation of Formulations Containing Category (b) Agents

1. Weigh out the appropriate amount of hydrophobic bioactive (e.g. progesterone, 5–6 g) into a container.

2. Add solvent (e.g. propylene glycol, 35 g) to the container.

3. Add an oil solvent (e.g. benzyl alcohol, 19–20 g) and mix well until all the drug has dissolved.

4. Dissolve a small amount of polymer (Carbopol 934P, 0.7–0.8 g) in second portions of solvent (e.g. dimethylacetamide, 40 g) and add to product of step (3).

5. Add a neutralizing agent (e.g. triethanolamine, 0.3 to 0.35 g ) and mix well.

6. Add an emulsifying agent (e.g. Span 80, 1–1.2 g) and mix well.

Preparation of Formulations Containing Category (c) Agents

1. Measure the appropriate amount of solvent (e.g. propylene glycol, 50–55 g) into a container and stir with a magnetic stirrer so that a vortex is formed.

2. Slowly add the appropriate amount of polymer (e.g. Carbopol 934P, 0.7–0.8 g) into the vortex of solvent in the container slowly over a period of 5 minutes, stirring continuously to maintain vortex until the polymer is dissolved.

3. Add neutralizing agent (e.g. Triethanolamine, 1.4–1.6 g) to the solution and mix throughly. The system will become viscous at this stage.

4. Add an appropriate amount of a second portion of solvent (e.g. dimethylacetamide, 40–45 g) to above product and mix well.

5. Add oil solvent (e.g. benzyl alcohol or olive oil, 4–5 g) and mix well.

6. Add the desired amount of category (c) bioactive agent (e.g. 1,1 bis(p-chlorophenyl)-2,2,2-trichloroethanol 5–6 g) and mix well.

7. Add emulsifying agent (e.g. Tween 80, 2–3 g) and mix throughly.

The temperature range for the preparation of the formulations in accordance with the foregoing is from ambient temperature to about 70° C. or higher depending upon the thermal stability of the components. Heating Carbopol 934P, for example, above the 70° C. range can irreversibly degrade the polymer and result in loss of its viscosity-enhancement properties. Many drugs are also adversely affected by elevated temperatures.

The emulsions and/or solution of the present invention may be stable over extended periods of time (at least 4 months). Exposure to light may result in slight discoloration. Therefore, it is preferable to store the present compositions in opaque containers.

Experimental Results

In Vivo Studies Using Propranolol

Experiments were conducted to evaluate the efficacy of the bioactive agent delivery compositions of the present invention. Polymer formulations containing a drug as the bioactive agent were studied in a dog model to ascertain whether intranasal administration via the bioactive agent delivery compositions of the present invention increased bioavailability of the drug.

The drug selected was propranolol, an adrenergic drug which undergoes extensive first-pass metabolism in the liver, and therefore, has very low bioavailability when administered orally. Specific formulations used in the experiment are given below, expressed in terms of weight percentages:

Formulation 1

| | |
|---|---|
| 36.3% | Propylene Glycol |
| 40.6% | Dimethylacetamide |
| 1.7% | Span 80 |
| 4.4% | Olive Oil |
| 5.1% | Propranolol |
| 1.7% | Carbopol 934P |
| 10.2% | Triethanolamine |

Formulation 2

| | |
|---|---|
| 35.9% | Propylene Glycol |
| 41.1% | Dimethylacetamide |
| 1.4% | Span 80 |
| 4.3% | Benzyl Alcohol |
| 5.2% | Propranolol |
| 1.7% | Carbopol 934P |
| 10.4% | Triethanolamine |

The experiments were carried out on male beagle dogs, each roughly 10 kg in weight. The dogs were fasted overnight before each study and food was withheld until the end of the experiment. The dogs were restrained in a dog sling. Approximately 10 mg of propranolol was administered nasally to each dog by spraying an appropriate amount of the present formulations containing propranolol into both nostrils of the dog using a metered dose dispenser (typically 2 sprays over a two minute period). The amount of drug administered nasally was obtained by weighing the dispenser before and after spraying.

Blood samples were withdrawn at desired intervals from each dog through a cannula inserted in the cephalic vein. The blood samples were centrifuged immediately after the collection and the plasma samples were stored frozen until assayed. The assay for propranolol consisted of HPLC separation and UV/fluorescence detection.

Figure 8:
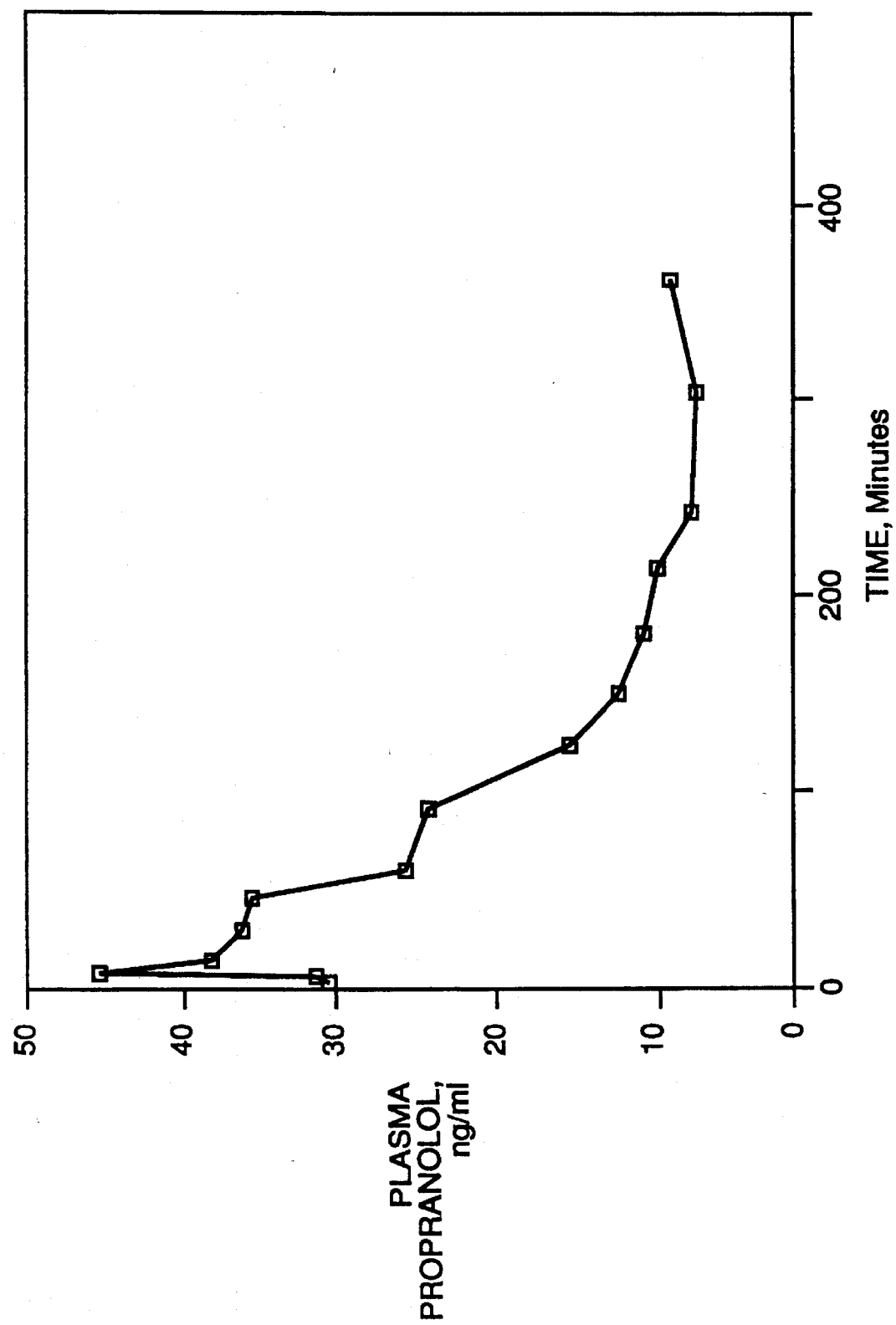
FIGS. 8 and 9 are graphical plots of plasma level of drug (ng/ml) versus time for the nasal administration of propranolol to two dogs via a specific, illustrative embodiment of a drug delivery system in accordance with the present invention.
Figure 9:
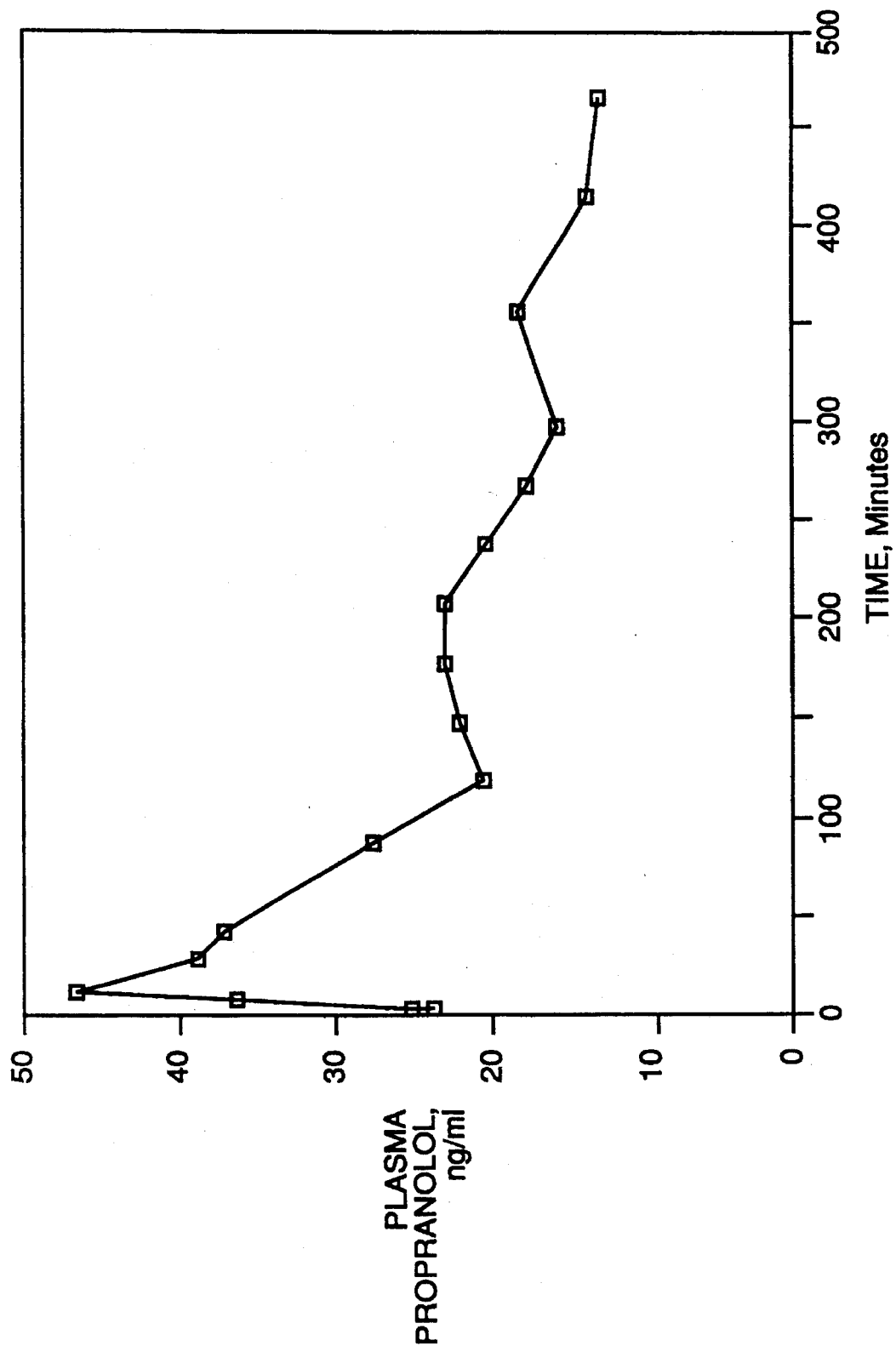
Figure 10:
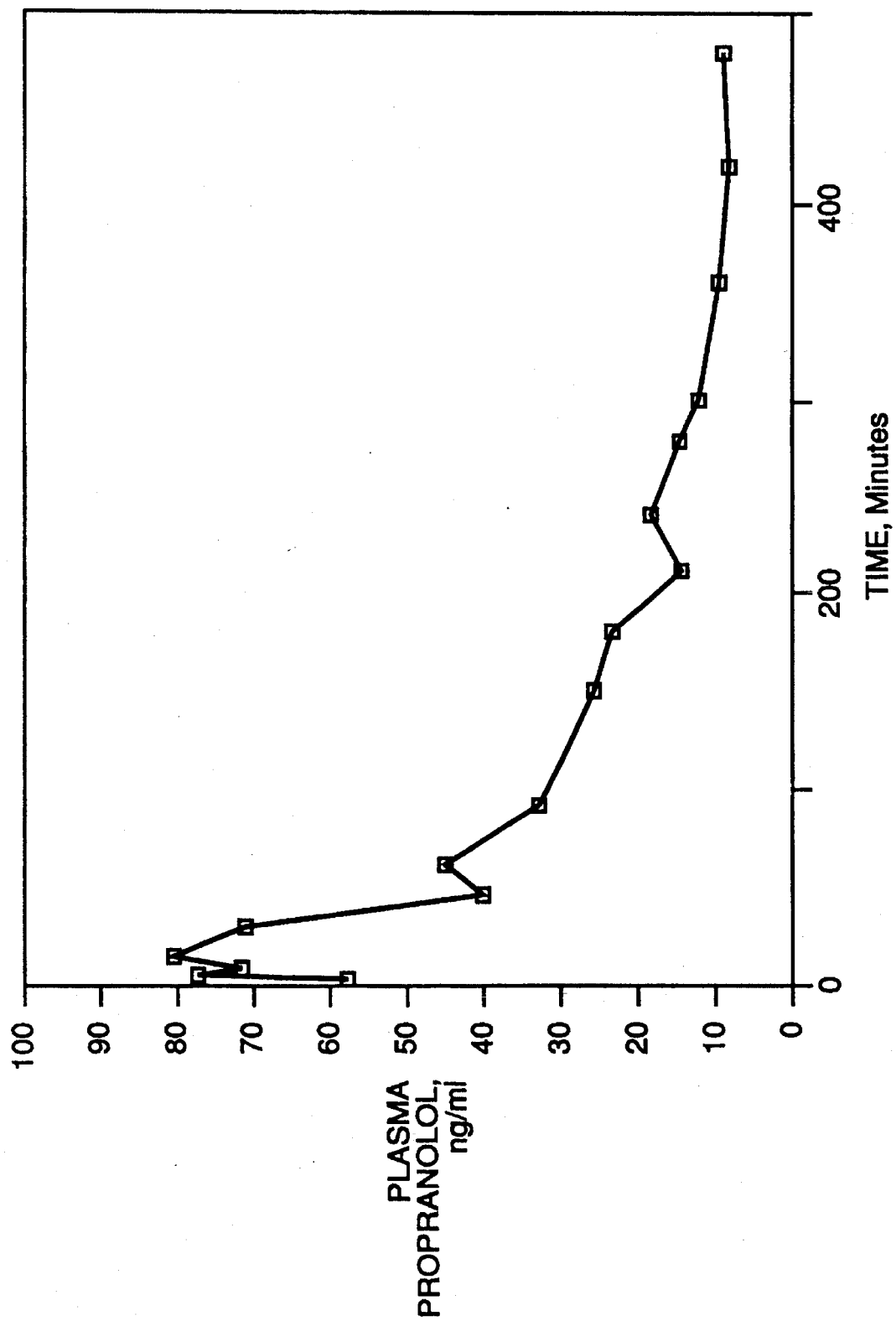
FIGS. 10 and 11 are graphical plots of plasma level of drug (ng/ml) versus time for the nasal administration of propranolol to two dogs of another specific, illustrative embodiment of a drug delivery system in accordance with the present invention.
Figure 11:
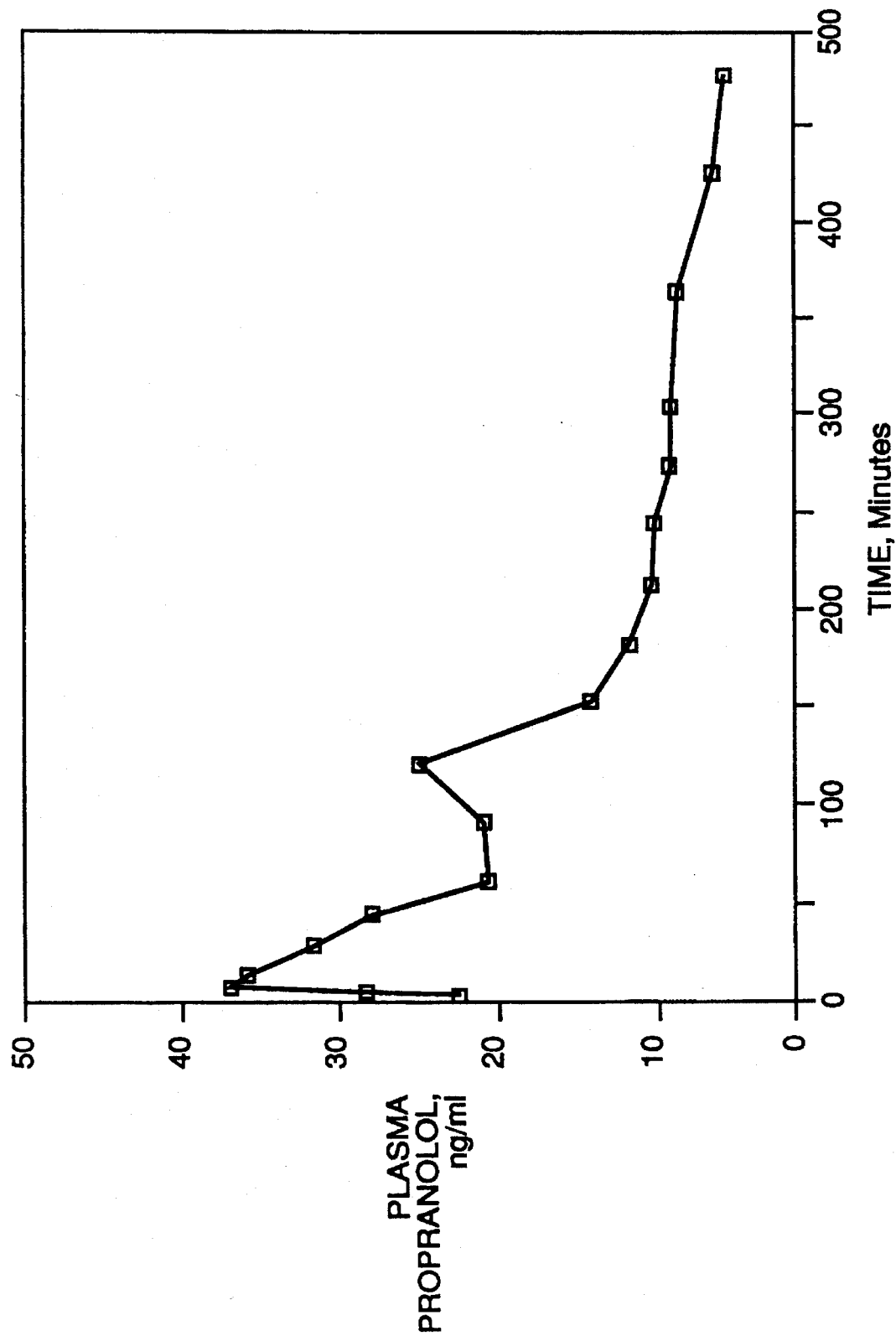

FIGS. 8 through 11 are plots of plasma level (ng/ml) of drug versus time curves. Specifically, FIGS. 8 and 9 are graphical plots of the plasma level of propranolol as a function of time for two dogs following nasal administration of the propranolol delivery system of Formulation 1. FIGS. 10 and 11 are graphical plots of the plasma level of propranolol versus time for the same two dogs following nasal administration of the propranolol delivery system of Formulation 2.

The bioavailability of propranolol is listed in Table 7 which represents a comparison of relevant pharmacokinetic parameters for intravenous (IV), nasal, and oral administration of propranolol to the dogs.

TABLE 7

BIOAVAILABILITY OF PROPRANOLOL

| Route | Formulation | C max (ng/ml) | T max (min) | AUC/IV-AUC 0–8 Hours |
|---|---|---|---|---|
| IV | Saline | 185 | 3 | 1.00 |
| Nasal | 1 | 46 | 15 | 0.33 |
| Nasal | 2 | 59 | 15 | 0.37 |
| Oral | Tablet | 3 | 120 | 0.04 |

As shown in Table 7, the nasal bioavailability is presented as a fraction of the bioavailability of an equivalent dose of propranolol (10 mg) administered intravenously. The area under the curve (AUC) has been normalized to the amount of propranolol administered. It is evident from the results that the enhancement in bioavailability of propranolol administered nasally using the formulations of the present invention is about ten-fold greater than that obtained by oral administration of propranolol in tablet form.

In Vivo Studies Using Progesterone

As a specific example of a bioactive agent delivery system containing a category (b), or hydrophobic, drug, the following composition incorporating progesterone as the bioactive agent was produced. This formulation was tested in vivo for blood level in comparison to a non-aqueous solution of progesterone (Formulation 4) which was not prepared in accordance with the principles of the invention and which, therefore, does not exhibit the advantageous viscosity augmentation characteristic of Formulation 3 upon administration to the mucosa.

Formulation 3

| Ingredient | Weight % |
|---|---|
| Propylene Glycol | 35.00 |
| Dimethylacetamide | 39.00 |
| Benzyl Alcohol | 18.90 |
| Carbopol 934P | 0.66 |
| Triethanolamine | 0.33 |
| Span 80 | 1.11 |
| Progesterone (Micronized) | 5.00 |

Formulation 3 was produced by dissolving progesterone in a solvent system of propylene glycol and benzyl alcohol. The Carbopol 934P polymer was dissolved in dimethylacetamide and combined with the progesterone-containing solution. Triethanolamine and Span 80 were then added to form a fluid, low viscosity emulsion.

Formulation 4

| Ingredient | % W/V |
|---|---|
| Progesterone USP (Micronized) | 5.0 |
| Benzyl alcohol N.F. | 1.6 |
| Glycerol monoleate/propylene glycol qs to | 500 ml |

Test formulations 3 and 4 were administered into the nostrils of four male beagles in an atomized form on three separate days to assess the absorption of the formulations by the mucosa. The dogs received two sprays in each nostril (10 mg) and blood samples were withdrawn and analyzed as set forth in the propranolol studies discussed hereinabove. The nostrils of the dogs were examined before dosing and following dosing at the same intervals at which the blood samples were obtained for the progesterone assays. No nasal irritation was observed in the progesterone treated animals.

Figure 12:
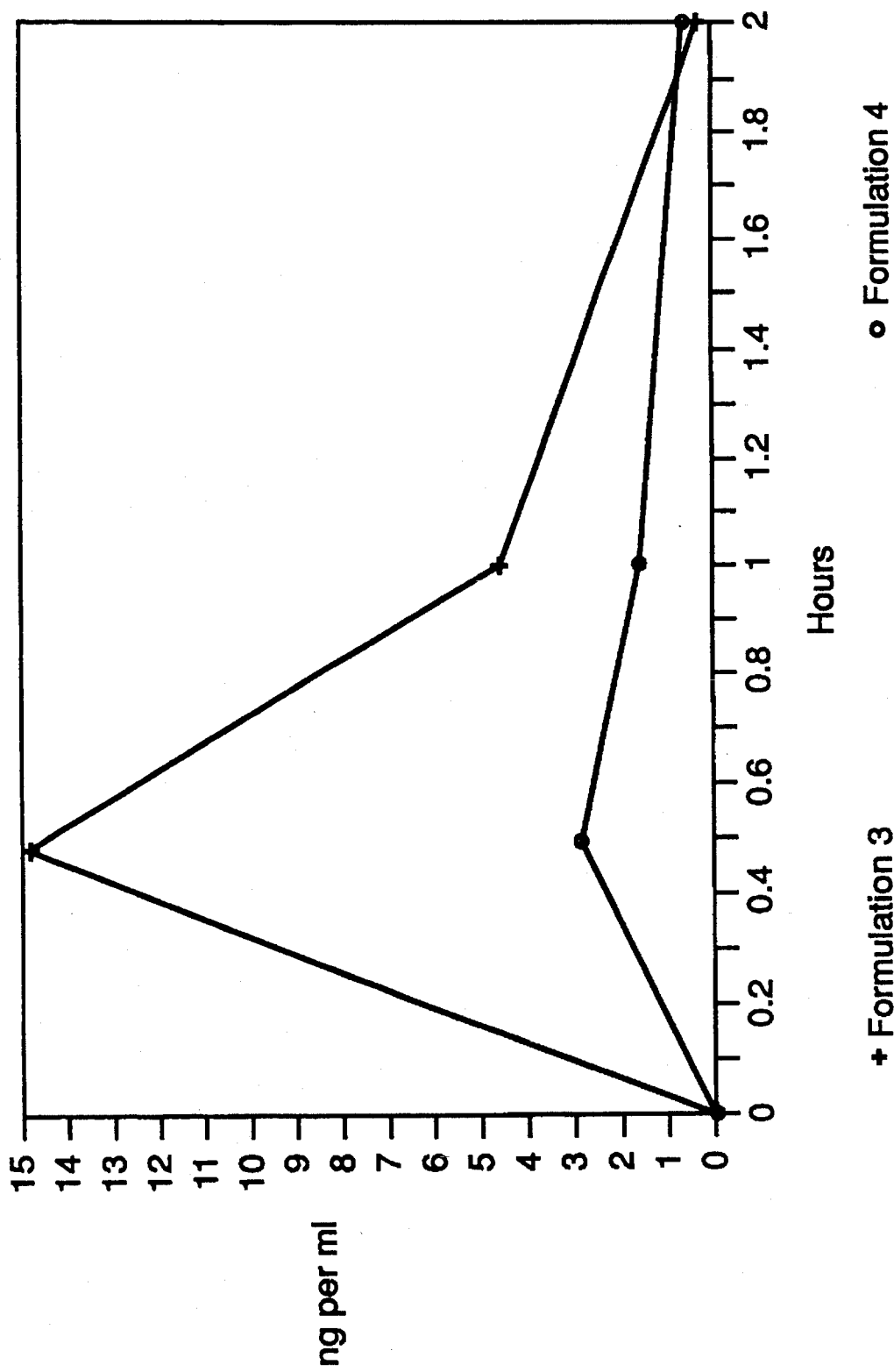
FIG. 12 is a graphical plot of plasma level of drug (ng/ml) versus time over a two hour period after intranasal administration of progesterone to two dogs via a drug delivery of the present invention.

FIG. 12 shows the plasma levels of progesterone in ng/ml versus time over a two hour period post dosing for Formulations 3 and 4. FIG. 12 graphically demonstrates the superior bioavailability achievable by use of the novel progesterone delivery system of the present invention.

Plant Study Using Miticide

Comparative formulations of a miticide solution for use in the protection of plant foliage were prepared. They differed essentially by whether or not they contained Carbomer 934P so as to comprise a bioactive agent delivery composition in accordance with the present invention. Their formulas were as follows:

| Ingredient | Weight | |
|---|---|---|
| | Active(A) | Placebo(B) |
| Keltane EC | 1.0 | 1.0 |
| Dimethyl Acetamide | 45.4 | 45.8 |
| Propylene Glycol | 45.4 | 45.8 |
| Benzyl Alcohol | 4.9 | 4.9 |
| Carbomer 934P | 0.8 | — |
| Triethanolamine | 1.1 | 1.1 |
| Span 80 | 1.4 | 1.4 |
| | 100.0 | 100.0 |

The formulation of Formula A was prepared in accordance with the present invention by forming a first solution by dissolving the Keltane EC in benzyl alcohol and then adding the propylene glycol. Separately, the Carbomer 934P was slowly added to the dimethyl acetamide in a magnetic stirrer to form a second solution. After combining the solutions, while continuing mixing, the triethanolamine and Span 80 were added sequentially.

The formulation of Formula B (the placebo or control to Formula A) was prepared in the same manner, except for omission of the step of adding the Carbomer 934P. To compare the relative effectiveness of these two formulations, squares (10 cm by 10 cm) were cut from the center of peace lily leaves. These test squares were then placed in a humidifier (Model HC 22, Soundesign, Jersey City, N.J.) and exposed to maximum humidification (6 mL/min) for 5 minutes.

Thereafter, the top surfaces of the test squares were sprayed with 0.1 mL respectively of Formula A or B. This deposited 105 mg of formula on each square. The test squares were then placed 10 centimeters in front of the humidifier spout, arranged so that their planes formed an angle of 45 degrees from the horizontal. The humidifier was then operated at maximum with its output stream being directed onto the top surfaces of the test squares. The condensed drippings from the test square surfaces were monitored periodically for 24 hours by ultraviolet spectroscopic analysis for miticide washed from the leaf test squares. The results of these periodic analyses were as follows:

| Time | Formula A Amount Released | | | Formula B Amount Released | | |
|---|---|---|---|---|---|---|
| Hours | mg. | Cumul. mg. | Cumul. % | mg | Cumul. mg. | Cumul. % |
| 0 | — | — | 0 | — | — | 0 |
| 1 | 6.0 | 6.0 | 5.7 | 64.9 | 64.9 | 61.8 |
| 3 | 16.6 | 22.6 | 21.5 | 3.2 | 68.1 | 64.8 |
| 5 | 4.4 | 27.0 | 25.7 | 1.4 | 69.4 | 66.1 |
| 7 | 2.2 | 29.2 | 27.8 | 1.4 | 70.8 | 67.4 |
| 24 | 2.5 | 31.7 | 30.2 | 1.4 | 72.2 | 68.8 |

This Example provides an accelerated showing of the differences which such plant formulations would exhibit in nature. Humidification simulates the effect on leaf treatments which results from dew, fog or even light rain.

Figure 13:
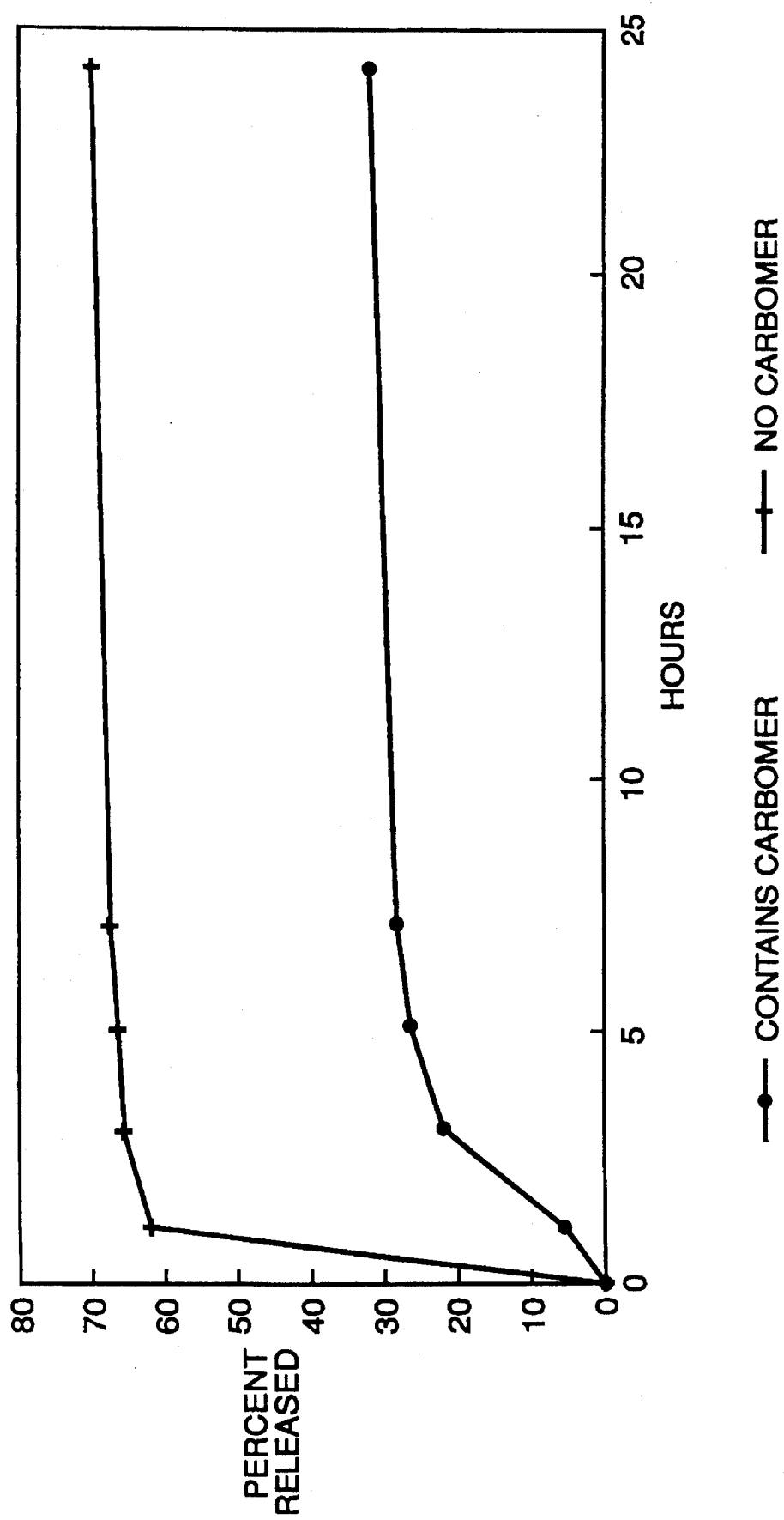
FIG. 13 is a graphical of the percent of release or loss of miticide from leaf samples versus time over a twenty-four hour accelerated aging study on compositions with and without a hydrophilic polymer of the present invention.

The data from this example is graphically depicted in FIG. 13. Several of the advantages of the present invention are clearly evident from the relative amounts of miticide released or washed from the leaf over time.

From FIG. 13, it is apparent that the placebo or control sample, Formula B, which omits a hydrophilic polymer of the present invention, undergoes an almost immediate loss of over 60% of applied miticide. In contrast, Formula A conforming to the present invention undergoes only a significantly smaller immediate loss of miticide from the leaf squares and thereafter continues to reflect a cumulative loss which is less than one-half that of the control.

After exposing the leaf squares to this humidification, they were separately rinsed in wash streams of 50:50 ethanol-water. This removed the respective topical residue of each formulations. Analysis showed that the recoverable residues were: Formula (A), 43.9 mg; and Formula (B), 4.0 mg. Thus, after 24 hours of humidification, hydrophilic polymer of the present invention is responsible for an eleven (11) fold increase in topical retention.

The foregoing also permitted calculation of formulation which penetrated into the leaves. Both sets of samples were originally dosed with A 105 mg of formulation. Subtracting the amounts respectively removed incident 24 hour humidification and wash, it is seen that the leaf squares absorbed approximately equal amounts—29.4 mg of Formula A and 28.8 mg of Formula B. Significantly this evidences the fact that the present invention need not interfere with penetration into a substrate, even while assuring improved surface retention.

Figure 14:
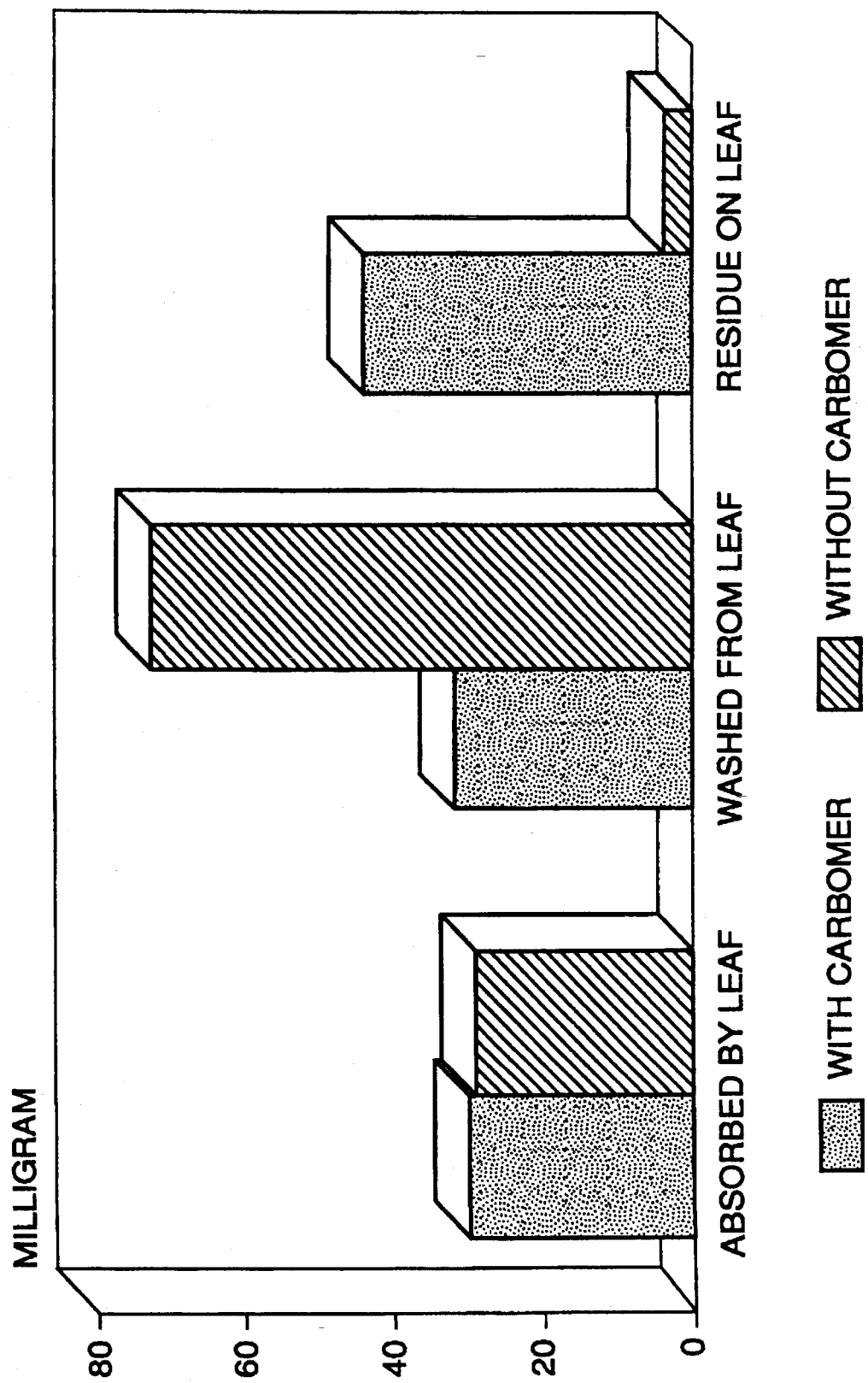
FIG. 14 is a compound bar graph illustrating the relative distributions of absorbed, washed or residual miticide formulations of the foregoing study after aging.

The results of this Example are depicted in FIG. 14. On this bar graph the relative amounts of each formula which are absorbed into, washed from, and retained on the leaf squares are shown.

The advantages attendant the foregoing are obvious and substantial. Given its relatively reduced release or loss rate, the present invention affords a method of plant treatment which will achieve a given effect both at a lower application level for the bioactive agent and over a lengthened period of effective bioactivity on a plant. Thus, the bioactive agent can be more economically utilized, with reduced danger of adverse ecological impact beyond its desired site of activity.

It is to be understood that the present invention can be used to administer a wide variety of bioactive agents too numerous to mention. Some of the bioactive agents which are drugs, and which can be delivered using the present invention include, without limitation, analgesic and anti-inflammatory agents, anti-inflammatory enzyme preparations, anti-inflammatory steroids, antihistamines, antibiotics, antibacterial agents, chemotherapeutic agents, local anesthetics, cardiac tonics, vasodilators, antitussive and expectorants, oral antiseptics, hemostats, hormones, hypotensive agents, sedative or tranquilizers, anti-tumor agents, gastrointestinal drugs and antacids.

Specific illustrative drugs which may be employed in the practice of the invention include, but are not limited to, acetaminophen, phenacetin, aspirin, aminopyrine, sulpyrine, phenabuazone, mefenamic acid, flufenamic acid, Ibufenac, Ibuprofen, indomethacin, colchicine, and Probenecid, anti-inflammatory enzymes, such as alpha-chymotrypsin, anti-inflammatory steroids, such as hydrocortisone, prednisone, prednisolone, triamcinolone, diamethasone, and betamethasone; antihistamines, such as diphenyldramine hydrochloride and dexchlorpheniramine maleate; antibiotics, such as tetracycline hydrochloride, leucomycin, fradiomycin, penicillin and its derivatives, cephalosporin derivatives and erythromycin; antibacterial agents; chemotherapeutic agents, such as sulfathiosole and nitrofurazone; local anesthetics, such as benzocaine; cardiac tonics, such as digitalis and digoxin; vasodilators, such as nitroglycerin and papaverine hydrochloride; antitussive and expectorants, such as codeine phosphate and isoproterenol hydrochloride; oral antiseptics, such as chlorhexidine hydrochloride and hexylresorcinol; drugs for the digestive organs such as pepstatin; hypoglycemics, such as insulin; hemostats; sex hormones; hypotensive agents; sedative or tranquilizers; anti-tumor agents; gastrointestinal drugs and antacids. It should be noted that the bioactive agents may be used singly or as a mixture of two or more such agents, and in amounts sufficient to prevent, cure, or treat a disease, as the case may be, to which the pharmaceutical preparation delivered in accordance with the principles of the invention is to be applied.

Although the invention has been described most specifically in terms of intranasal administration of a drug, the bioactive agent delivery composition of the present invention is applicable to other routes of drug administration such as transdermal, parenteral, rectal, vaginal, ophthalmic, otic, etc.

As previously noted, the present invention is not limited in its application to uses in relation to the application of a drug or medicament to a living being. It is broadly useful to the delivery of a wide variety of bioactive agents in the practice of many other fields which would benefit from a post-delivery increase in the viscosity of the delivered material to achieve and enhance the bioeffect of the applied agents or the duration of an application thereof. Illustrative other "bioactive agents" include, all plant treatment chemicals such as pesticides; non-therapeutic materials which are applied to the surfaces of the bodies of living beings, such as cosmetic agents, sun screens, skin softeners, acne treating agents, perfumes, etc. In addition, certain foods or other ingestibles can be protected with a coating which is applied in liquid form, but which gels to produce a protective layer which excludes air and may incorporate other materials such as preservatives, antioxidants, and nutritional agents, such as vitamins and/or minerals.

Although the invention has been described in terms of specific embodiments and applications, persons skilled in the art can, in light of these teachings, generate additional embodiments without exceeding the scope or departing from the spirit of the claimed invention. Accordingly, it is to be understood that the drawings and description in this disclosure are proffered to facilitate comprehension of the invention, and should not be construed to limit the scope thereof.

What is claimed is:

1. A bioactive composition comprising:
   a. bioactive agent;
   b. hydrophilic polymer in an incompletely hydrated state; and
   c. substantially water-miscible solvent system; said system maintaining said agent and polymer in essentially dissolved form whereby said composition has a viscosity of less than 350 cP, which viscosity increases to in excess of 1000 cP upon dilution with water.

2. The bioactive agent delivery composition of claim 1 wherein the hydrophilic polymer is an ionic polymer.

3. The bioactive agent delivery composition of claim 1 wherein the hydrophilic polymer is a neutral polymer.

4. The composition of claim 1 wherein the hydrophilic polymer is a salt of an acidic ionic polymer and a neutralizing agent selected from the group consisting of inorganic bases and organic amines.

5. The composition of claim 4 wherein the neutralizing agent is an organic amine and is selected from the group consisting of triethanolamine, diisopropanolamine, monoethanolamine, basic amino acids and amine surfactants.

6. The composition of claim 1 wherein the hydrophilic polymer is a salt of a basic polymer and an inorganic acid neutralizing agent.

7. The composition of claim 1 wherein the solvent system comprises polypropylene glycol.

8. The composition of claim 1 wherein the solvent system comprises non-aqueous, pharmaceutically approved, parenteral vehicle.

9. The composition of claim 8 wherein the non-aqueous, pharmaceutically approved, parenteral vehicle is selected from the group consisting of dimethylacetamide, ethyl lactate, ethyl carbonate, dimethylformamide, dimethyl sulfoxide, and dioxolanes.

10. The composition of claim 1 wherein the solvent system comprises an organic solvent and an oil solvent.

11. The composition of claim 10 wherein the oil solvent is a hydrophobic organic substance.

12. The composition of claim 10 wherein the oil solvent is selected from the group consisting of fixed oils, and essential oils.

13. The composition of claim 1 which additionally comprises an emulsifying agent.

14. The composition of claim 13 wherein the emulsifying agent comprises a non-ionic surfactant of HLB less than about 15.

15. The composition of claim 1 wherein the hydrophilic polymer is selected from the group consisting of homopolymer of acrylic acid monomer, copolymers of acrylic acid; vinyl polymer; poly(ethylene oxide) polymers; cellulose derivatives; and the non-toxic, pharmaceutically acceptable salts of these polymers.

16. The composition of claim 15 wherein the hydrophilic polymer is an acrylic acid copolymer, the acrylic acid copolymer being present in an amount of approximately between 0.6 and 2 percent by weight of the composition.

17. The composition of claim 16 wherein the hydrophilic polymer is a salt of an organic amine selected from the group consisting of triethanolamine, diisopropanolamine, monoethanolamine, basic amino acids and amine surfactants and is present in an amount approximately between 0.3 and 10 percent by weight of the composition.

18. The composition of claim 17 wherein the bioactive agent is present in an amount between approximately 2 and 10 percent by weight of the composition.

19. The composition of claim 17 wherein the solvent system comprises a first, water-miscible organic solvent and a second, oil solvent present in an amount of up to approximately 30 percent by weight of the composition.

20. The composition of claim 1 wherein the bioactive agent is a drug.

* * * * *